US009579426B2

(12) United States Patent
Chen et al.

(10) Patent No.: US 9,579,426 B2
(45) Date of Patent: *Feb. 28, 2017

(54) COATED ELASTOMERIC ARTICLE

(71) Applicant: ALLEGIANCE CORPORATION, Waukegan, IL (US)

(72) Inventors: Seong Fong Chen, Gelugor (MY); Shiping Wang, Libertyville, IL (US); Wei Cheong Wong, Kulim (MY); Chuang Sim Chong, Greenlane (MY)

(73) Assignee: ALLEGIANCE CORPORATION, Waukegan, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,635

(22) Filed: Jun. 4, 2015

(65) Prior Publication Data

US 2015/0342274 A1 Dec. 3, 2015

Related U.S. Application Data

(63) Continuation of application No. 13/347,336, filed on Jan. 10, 2012, now Pat. No. 9,080,025, which is a continuation of application No. 11/672,705, filed on Feb. 8, 2007, now Pat. No. 8,110,266.

(51) Int. Cl.
| | | |
|---|---|---|
| A61L 31/10 | (2006.01) | |
| A61L 31/14 | (2006.01) | |
| A61L 29/08 | (2006.01) | |
| A61L 29/14 | (2006.01) | |
| C08J 5/00 | (2006.01) | |
| A41D 19/00 | (2006.01) | |
| B32B 1/08 | (2006.01) | |
| B32B 1/00 | (2006.01) | |
| C08J 7/04 | (2006.01) | |

(52) U.S. Cl.
CPC .......... *A61L 31/10* (2013.01); *A41D 19/0058* (2013.01); *A41D 19/0068* (2013.01); *A61L 29/085* (2013.01); *A61L 29/14* (2013.01); *A61L 31/14* (2013.01); *B32B 1/00* (2013.01); *B32B 1/08* (2013.01); *C08J 5/00* (2013.01); *C08J 7/047* (2013.01); *A61L 2420/02* (2013.01); *C08J 2307/02* (2013.01); *C08J 2321/02* (2013.01); *C08J 2409/00* (2013.01); *Y10T 428/13* (2015.01); *Y10T 428/1334* (2015.01); *Y10T 428/1352* (2015.01); *Y10T 428/1379* (2015.01); *Y10T 428/1386* (2015.01); *Y10T 428/1393* (2015.01); *Y10T 428/24355* (2015.01); *Y10T 428/31855* (2015.04)

(58) Field of Classification Search
CPC ......... B32B 1/00; B32B 1/08; A41D 19/0068; A61L 29/085; A61L 29/14; A61L 31/10; A61L 31/14; Y10T 428/1386; Y10T 428/1393; Y10T 428/31855
See application file for complete search history.

(56) References Cited

U.S. PATENT DOCUMENTS

| | | | |
|---|---|---|---|
| 3,250,737 A | 5/1966 | Halper et al. | |
| 3,285,869 A | 11/1966 | Ronay et al. | |
| 3,565,870 A | 2/1971 | Hirokazu | |
| 3,813,695 A | 6/1974 | Podell et al. | |
| 3,846,365 A | 11/1974 | Berg et al. | |
| 3,968,067 A | 7/1976 | Burke, Jr. | |
| 3,971,746 A | 7/1976 | Hirai et al. | |
| 4,143,109 A | 3/1979 | Stockum | |
| 4,452,879 A | 6/1984 | Fickes et al. | |
| 4,463,120 A | 7/1984 | Collins et al. | |
| 4,499,154 A | 2/1985 | James et al. | |
| 4,575,476 A | 3/1986 | Podell et al. | |
| 4,594,367 A | 6/1986 | Geissel et al. | |
| 4,849,478 A | 7/1989 | Mori et al. | |
| 5,039,750 A | 8/1991 | Miller et al. | |
| 5,073,365 A * | 12/1991 | Katz | A61F 13/00 424/484 |
| 5,088,125 A | 2/1992 | Ansell et al. | |
| 5,155,163 A | 10/1992 | Abeywardena et al. | |
| 5,254,635 A | 10/1993 | Stevenson et al. | |
| 5,284,607 A | 2/1994 | Chen | |
| 5,395,666 A | 3/1995 | Brindle | |
| 5,405,666 A | 4/1995 | Brindle | |

(Continued)

FOREIGN PATENT DOCUMENTS

| | | |
|---|---|---|
| DE | 2135266 A1 | 1/1973 |
| EP | 1709879 A2 | 10/2006 |

(Continued)

OTHER PUBLICATIONS

ASTM Standard D 1076-02. "Standard Specification for Rubber—Concentrated, Ammonia Preserved, Creamed, and Centrifuged Natural Latex," published in Sep. 2002. pp. 218-219.
Aughenbaugh, Walter, Non-Final Office Action mailed Apr. 11, 2016 for U.S. Appl. No. 14/730,635, 16 pages.
Aughenbaugh, Walter., Office Action mailed on May 8, 2014 in U.S. Appl. No. 13/347,357,35 pages.
Blackley D.C., High Polymer Latices, 1966, vol. 1, Maclaren & Sons Ltd., Palmerton Publishing Co. Inc., New York, pp. 336-337.
Chen F. B. "Synthetic Polyisoprene Latex," 3rd International Rubber Glove Conference & Exhibition. Sep. 12-14, 2006, Kuala Lumpur, Malaysia. pp. 1-19.
David L.N., et al., Lehninger Principles of Biochemistry, 2004, Fourth Edition, Chapter 10, Freeman W.H., pp. 344-345.

(Continued)

*Primary Examiner* — Walter B Aughenbaugh
(74) *Attorney, Agent, or Firm* — Nicole M. Gratzer; Amanda F. Maharaj

(57) ABSTRACT

This invention relates to an elastomeric article with improved lubricity and donnablity and reduced stickiness/tackiness. According to the methods of the invention, the internal surface of the elastomeric article is coated with a polyisoprene coating. The coating of the invention is formed from synthetic polyisoprene rubber that may or may not contain minor amounts of other components. The coating is preferably directly bonded to the underlying elastomeric article.

26 Claims, 8 Drawing Sheets

(56) References Cited

U.S. PATENT DOCUMENTS

| | | | |
|---|---|---|---|
| 5,459,880 A | 10/1995 | Sakaki et al. | |
| 5,545,451 A | 8/1996 | Haung et al. | |
| 5,670,263 A | 9/1997 | Gazeley | |
| 5,792,531 A | 8/1998 | Littleton et al. | |
| 5,910,567 A | 6/1999 | Tanaka et al. | |
| 5,993,923 A | 11/1999 | Lee | |
| 6,000,061 A | 12/1999 | Taneja et al. | |
| 6,075,073 A | 6/2000 | McGlothlin et al. | |
| 6,143,416 A * | 11/2000 | Brindle | B29C 33/424 |
| | | | 2/161.8 |
| 6,263,249 B1 | 7/2001 | Stewart et al. | |
| 6,329,444 B1 | 12/2001 | McGlothlin et al. | |
| 6,365,278 B1 | 4/2002 | Hoerner et al. | |
| 6,391,409 B1 | 5/2002 | Yeh et al. | |
| 6,560,782 B2 | 5/2003 | Hourihan et al. | |
| 6,566,435 B1 | 5/2003 | Teoh et al. | |
| 6,582,788 B2 | 6/2003 | Yeh | |
| 6,618,861 B2 | 9/2003 | Saks et al. | |
| 6,673,404 B1 | 1/2004 | Yeh et al. | |
| 6,737,469 B2 | 5/2004 | Takamura et al. | |
| 6,746,562 B2 * | 6/2004 | Chino | C08J 3/24 |
| | | | 156/308.2 |
| 6,764,731 B2 | 7/2004 | Savoca et al. | |
| 6,794,475 B1 | 9/2004 | Bialke et al. | |
| 6,828,387 B2 | 12/2004 | Wang et al. | |
| 6,887,542 B2 | 5/2005 | Conley et al. | |
| 7,037,579 B2 | 5/2006 | Hassan et al. | |
| 7,335,807 B2 | 2/2008 | Hochgesang | |
| 7,566,502 B1 | 7/2009 | Chen et al. | |
| 8,062,755 B2 | 11/2011 | Chen et al. | |
| 8,110,266 B2 * | 2/2012 | Chen | A41D 19/0058 |
| | | | 2/161.7 |
| 8,835,014 B2 | 9/2014 | Wang et al. | |
| 9,080,025 B2 * | 7/2015 | Chen | A41D 19/0058 |
| 2002/0002227 A1 | 1/2002 | Porter et al. | |
| 2002/0015812 A1 | 2/2002 | Littleton et al. | |
| 2002/0029402 A1 | 3/2002 | Yeh | |
| 2002/0133864 A1 | 9/2002 | Saks et al. | |
| 2002/0173563 A1 * | 11/2002 | Wang | C08J 5/02 |
| | | | 524/25 |
| 2004/0071909 A1 | 4/2004 | McGlothlin et al. | |
| 2004/0091504 A1 | 5/2004 | Hamann | |
| 2004/0091557 A1 | 5/2004 | Hamann | |
| 2004/0126604 A1 | 7/2004 | Wang et al. | |
| 2004/0169317 A1 | 9/2004 | Wang et al. | |
| 2005/0031884 A1 | 2/2005 | Koide et al. | |
| 2006/0010565 A1 | 1/2006 | Teoh et al. | |
| 2006/0059604 A1 | 3/2006 | Lai et al. | |
| 2006/0099237 A1 | 5/2006 | Modak et al. | |
| 2006/0108718 A1 | 5/2006 | Miyamoto et al. | |
| 2006/0134613 A1 | 6/2006 | Martin et al. | |
| 2006/0141186 A1 | 6/2006 | Janssen et al. | |
| 2006/0222688 A1 | 10/2006 | Weiss et al. | |
| 2006/0257674 A1 | 11/2006 | Lipinski et al. | |
| 2008/0190322 A1 | 8/2008 | Chen et al. | |
| 2009/0234064 A1 | 9/2009 | Wang et al. | |
| 2009/0255033 A1 | 10/2009 | Chen et al. | |
| 2011/0178234 A1 | 7/2011 | Wang et al. | |
| 2012/0121838 A1 | 5/2012 | Chen et al. | |

FOREIGN PATENT DOCUMENTS

| | | |
|---|---|---|
| EP | 1935925 A1 | 6/2008 |
| GB | 2411101 A | 8/2005 |
| JP | S5150340 A | 5/1976 |
| JP | H059529 U | 2/1993 |
| JP | H0666688 U | 9/1994 |
| JP | H1161527 A | 3/1999 |
| JP | 2002522272 A | 7/2002 |
| JP | 2002309043 A | 10/2002 |
| JP | 2007501144 A | 1/2007 |
| JP | 2007514575 A | 6/2007 |
| JP | 2009209229 A | 9/2009 |
| WO | 0009320 A1 | 2/2000 |
| WO | 0190236 A1 | 11/2001 |
| WO | 02090430 A1 | 11/2002 |
| WO | 2004093690 A1 | 11/2004 |
| WO | 2004105525 A1 | 12/2004 |
| WO | 2005068186 A1 | 7/2005 |
| WO | 2008097643 A2 | 8/2008 |
| WO | 2009114788 A2 | 9/2009 |

OTHER PUBLICATIONS

European Search Report and Search Opinion for European Patent Application No. 08725350.6, mailed Apr. 19, 2010, 6 pages.
European Search Report and Search Opinion for European Patent Application No. 13150983.8, mailed Mar. 18, 2013, 7 pages.
Genencor Fact Sheet, "Synthetic Polyisoprene", downloaded on Jan. 26, 2010 from the internet: http://daniscosugar.com/cms/connect/genencor/products_and_services/business_devlopment/biochemicals/in_focus_bioisoprene/bioisoprene_en.htm, 2008, 7 pages.
Handbook of Preservatives by Michael and Irene Ash, 2004.
Henderson P., "From Isoprene monomer to synthetic polyisoprene latex and its uses," Presentation at Latex 2001, Dec. 4-5, 2001, Munich, Germany. pp. 77-90.
Henderson P., "Isoprene Monomer to Synthetic Polyisoprene Latex," International Latex Conference 2000, Jul. 25-26, 2000, Akron, Ohio, US, 8 pages.
Ho C.C. and Khew M.G., "Surface characterization of chlorinated unvulcanised natural rubber latex films," International Journal of Adhesion and Adhesives, 1999, vol. 19 (5), pp. 387-398.
International Search Report and Written Opinion for International Application No. PCT/US2008/001705, mailed Dec. 5, 2008, 5 pages.
International Search Report for Application No. PCT/US09/37130, mailed on May 18, 2009, 1 page.
Japanese Office Action for Japanese Patent Application No. 2010-550898, mailed Sep. 10, 2013.
Kraton. Carifiex(tm) IR latex compared to natural rubber latex, Jul. 2012, 15 pages.
Kraton, Cariflex(TM) Polysioprene Latex: Pure Performance and Comfort, 2011. 2 pages.
Kraton IR Polymers: The Clear Alternative, 2002. 2 pages.
Krylova Irina, Final Office Action mailed Jul. 10, 2015 for U.S. Appl. No. 11/811,641, 13 pages.
Krylova Irina, Non-Final Office Action mailed Dec. 18, 2014 for U.S. Appl. No. 11/811,641, 25 pages.
Mahmoud Abdei-Goad, et al., "Rheological Properties of 1,4-Polyisoprene over a Large Molecular Weight Range," Macromolecules, 2004, vol. 37 (21), pp. 8135-8144.
Mausser R.F., The Vanderbilt Latex Handbook, 3rd Edition, 1987, p. 109, R.T. Vanderbilt Company, Inc.,.
Natural Rubber Science and Technology, A.D. Roberts, ed., Oxford University Press, 1988, pp. 105-107.
Ngal K.L., et al., "Terminal Relaxation and Diffusion of Entangled Three-Arm Star Polymers: Temperature and Molecular Weight Dependencies," Journal of Polymer Science Part B: Polymer Physics, 1997, vol. 35 (15), pp. 2503-2510.
Office Action in corresponding Canadian Patent Application No. 2716805 mailed Jul. 4, 2016.
Office Action in corresponding Chinese Patent Application No. 2015-10117745 dated Jun. 27, 2016.
Office Action mailed Dec. 10, 2015 in corresponding European Patent Application No. 13150983.8, 3 pages.
Patent Examination Report No. 2, mailed in Australian Patent Application No. 2013204273 on May 14, 2015, 3 pages.
"Polyisoprene" Entry from Hawley's Condensed Chemical Dictionary, 14th Edition, © 2002, John Wiley & Sons, Inc. 1 page.
Product data sheet of NATSYN 2200 by GoodYear.
Substantive Examination Adverse Report and Search report mailed Mar. 15, 2016 for Malaysian Application No. PI2013003026, 3 pages.
Supplementary European Search Report for Application No. EP09721175, mailed on Feb. 15, 2011, 2 pages.
Tony Whelan, Polymer Technology Dictionary, 1994, Chapman & Hall, London, UK, p. 270.

(56) References Cited

OTHER PUBLICATIONS

Yildirim Erbil H., "Vinyl Acetate Emulsion Polymerization and Copolymerization with Acrylic Monomers," Chapter 7 Experimental Determination of Latex Properties, published in 2000 by CRC Press, 1 page.

* cited by examiner

COATED ELASTOMERIC ARTICLE

CROSS-REFERENCE TO RELATED APPLICATIONS

This application is a continuation of U.S. patent application Ser. No. 13/347,336, filed Jan. 10, 2012, granted as U.S. Pat. No. 9,080,025, which is a continuation of U.S. patent application Ser. No. 11/672,705, filed Feb. 8, 2007, granted as U.S. Pat. No. 8,110,266, issued Feb. 7, 2012. The disclosures of the prior applications are hereby incorporated by reference in their entirety.

FIELD OF INVENTION

The present invention relates generally to the field of medical and laboratory tools. More particularly, the invention relates to a coating composition for skin-contacting surfaces of medical and laboratory gloves.

BACKGROUND OF THE INVENTION

Medical and laboratory gloves often must be donned rapidly when used to perform time-sensitive medical procedures or laboratory experiments. Therefore, an important characteristic of these elastomeric articles is ease of putting the articles on the wearer's hand, or donnability. Additionally, articles such as medical gloves or condoms, for example, are anticipated to be worn by the user for extended periods of time. Because certain elastomeric articles are used with relatively higher frequency as well as with prolonged duration, important characteristics of such articles include their physical properties and their comfort of use.

A variety of medical gloves, e.g., surgical gloves and examination gloves, are well known and readily available in the medical field. The chemical and physical properties of elastomers used in such gloves have been researched, and gloves exhibiting desirable properties in accordance with their usage have been developed. Properties such as tensile strength and elongation modulus, as well as coatings and lubricants, which enhance their usage and/or donning characteristics, have been investigated. A variety of elastomeric polymer compositions have been examined as well, including formulations using natural and synthetic latex.

The manufacturing process for producing elastomeric articles from natural or synthetic rubber latex involves a curing step during which crosslinking or vulcanization through sulfur groups occurs between the polymer units. Conventional processes for making elastomeric articles from natural or synthetic latex typically involve preparing a latex dispersion or emulsion, dipping a former in the shape of the article to be manufactured into the latex and curing the latex while on the former. Desirable properties of certain elastomeric articles such as tensile strength are substantially affected by the cross-linking and curing stages of the manufacturing process.

Coating the inner surface of a glove is well-known in the art. U.S. Pat. No. 3,813,695 to Podell teaches coating a hydrophilic hydrogel plastic on the inner surface of a glove. U.S. Pat. No. 4,143,109 to Stockum discloses coating the inner surface of a glove with a layer comprising an elastomeric material having particulate matter randomly distributed throughout, the particulate matter having a size greater than the thickness of the elastomeric layer so that the particles protrude from the surface. In addition, U.S. Pat. No. 4,499,154 to James and U.S. Pat. No. 4,575,476 to Podell teach coating a hydrogel polymer to a rubber article to improve the dry skin lubricity where the hydrogel polymer is a copolymer of 2-hydroxyethylmethacrylate with methacrylic acid (MAA) or with 2-ethylhexyl acrylate (EHA) or with both MAA and EHA. U.S. Pat. No. 5,088,125 to Ansell discloses coating the hand contacting surface of a glove with an elastomeric material comprising a blend of an ionic polyurethane and a second particulate polymer having particle size greater than that of the ionic polyurethane which results in the surface having a cluster of particles on it. U.S. Pat. No. 5,284,607 to Chen teaches coating an elastomer surface with an antiblocking composition with particles distributed throughout, the majority of the particles having a size greater than the thickness of the antiblocking composition layer so that the particles form protrusions on the surface. U.S. Pat. Nos. 5,405,666 and 5,395,666 to Brindle teach coating an elastomeric article with a dry slip conferring coating which comprises a binder (a polymer with specific properties) and substantially nonaggregated microparticles (silica) of about 4 to about 20 micrometers such that the microparticles are enveloped by the binder but are partially protruding therefrom thus imparting to the surface a microroughened appearance. Finally, U.S. Pat. Nos. 6,391,409 and 6,673,404 to Yeh teach coating a natural rubber or synthetic elastomer glove on the skin-contacting surface with a cross-linked nitrile rubber blended with a silicone. Interposed between the nitrite rubber coating and the elastomeric glove is an intermediate layer of a rubber blend comprised of natural or synthetic rubber and nitrile rubber.

There exists a need in the medical device field for elastomeric articles, especially gloves, with improved donnability while maintaining the desirable properties found in the natural rubber counterpart, including a comfortable feel.

SUMMARY OF THE INVENTION

The present invention is based on the surprising discovery that a polyisoprene coated elastomeric article has physical properties (e.g., donnability, comfort, feel, surface stickiness) that are substantially improved when compared to an uncoated elastomeric article. This is true even when the polyisoprene is compared with materials that are very closely related chemically (e.g., natural rubber). Without being bound by mechanism, the improved characteristics are at least in part due to the chain flexibility of the polyisoprene segment.

The present invention provides for an elastomeric article having a coating formed from polyisoprene bonded thereto so as to provide an improved softness and donnability of the coated surface and reduce the stickiness/tackiness of the coated surface. Additionally, the invention provides for a rubber article having a coating formed from synthetic polyisoprene bonded thereto and treated with a lubricant solution on the coated surface of the article so as to provide an even further improved lubricity of the coated surface in both dry and wet donning conditions. The coated elastomeric product of the invention have a softer and more comfortable feel than an uncoated counterpart.

The invention also provides for a rubber article made from natural rubber, polyisoprene, polychloroprene, nitrile, carboxylated acrylonitrile butadiene rubber, styrene butadiene rubber, butadiene co-polymer, polyurethane or mixtures of these rubbers and vinyl. The synthetic polyisoprene rubber latex used for coating may contain a minor amount of natural rubber, polychloroprene latex, nitrile latex, carboxylated acrylonitrile butadiene rubber latex, styrene butadiene rubber, butadiene co-polymer or polyurethane latex or polyvinyl chloride (vinyl) latex.

The invention provides for a process of making an elastomeric article with a synthetic elastomeric polyisoprene coating.

DETAILED DESCRIPTION OF THE INVENTION

Figure 1A:
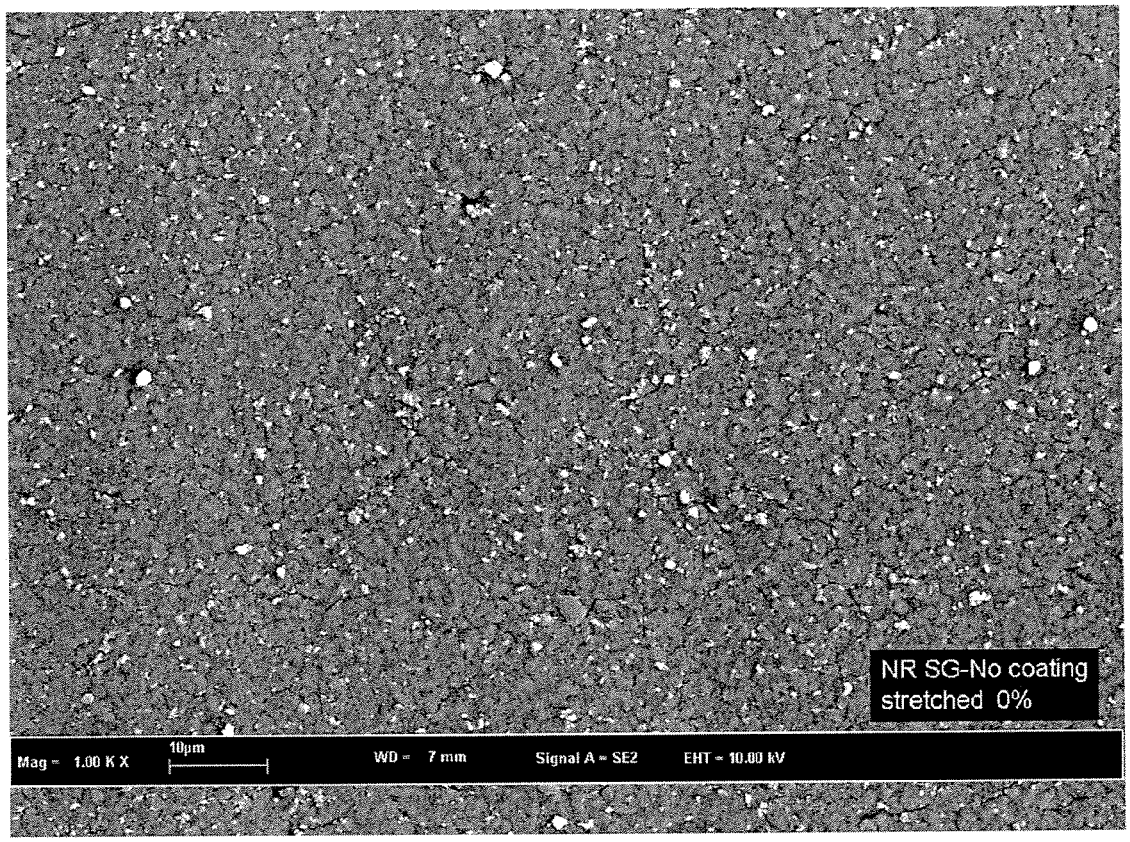
FIGS. 1A-1B show scanning electron micrographs taken on a natural rubber glove with no coating (A) without stretching or (B) after stretching 300% for 1 minute.

The object of the present invention is to provide a coating for the skin contacting surface of elastomeric articles that improves the lubricity and donnability of the article. The coating of the invention is formed from polyisoprene rubber latex that may or may not contain minor amounts of other components. The coating is preferably directly bonded to the underlying elastomeric article. The entire skin contacting surface may be coated with the polyisoprene coating of the invention or some portion thereof may be coated.

5.1 Elastomeric Article

A variety of elastomeric articles can be made in accordance with the invention. Such elastomeric articles include, but are not limited to, medical gloves, medical tubes, condoms, probe covers (e.g., for ultrasonic or transducer probes), dental dams, finger cots, catheters, films, shunts, valves, stents, implants, and the like. Any elastomeric article that would benefit from an improved lubricity of the coated surface and reduced stickiness/tackiness of the coated surface can be made using the methods of the invention since the invention provides numerous advantages and benefits in a number of ways with respect to donning. In preferred embodiments, donnable elastomeric articles comprise the coating of the invention. In more preferred embodiment, medical gloves comprise the coating of the invention.

In embodiments where the external surface of the elastomeric article comes into contact with the skin (e.g., catheter), the polyisoprene coating is on the external surface of the article.

The underlying elastomeric article can be made of any elastomeric composition, including but not limited to, polyisoprene, natural rubber, polychloroprene, nitrile, carboxylated acrylonitrile butadiene rubber, styrene butadiene rubber, butadiene co-polymer, polyurethane, vinyl or mixtures thereof. Additionally, in some embodiments, the elastomeric article can comprise a blend of a natural rubber material with at least one additional non-natural rubber glove material. Suitable examples of non-natural rubber glove materials include, but are not limited to, vinyl, nitrile, polyurethane, neoprene (polychloroprene), styrene butadiene rubber, butadiene co-polymer and combinations thereof. In preferred embodiments, the elastomeric article comprises polyisoprene, natural rubber, and/or neoprene.

In embodiments where the underlying elastomeric article is made of polyisoprene, the polyisoprene composition comprises the accelerator composition disclosed in U.S. Patent Publication No. 2004/0169317 (the contents of which are incorporated by reference in their entirety) to increase the rate of vulcanization of the polyisoprene.

5.2 Polyisoprene Coating

Any known polyisoprene latex composition can be used in the method of the invention to coat the surface of the elastomeric article including polyisoprene latex from natural sources (e.g., natural rubber, Guttapercha rubber, and Guayle rubber) and synthetic sources (e.g., water based latex or non-water based resin). The polyisoprene latex can be formulated or non-formulated. Polyisoprene latex is the major component of the coating composition. In preferred embodiments, the coating is greater than about 50%, about 60%, about 70%, about 75%, about 80%, about 85%, about 90%, about 95%, about 98%, or about 99% polyisoprene latex. Suitable polyisoprene latex which can be used is readily available and can be obtained from a number of commercial sources, including but not limited to, Kraton IR available from Kraton™ Corporation (Houston, Tex.).; Shell International Corporation (Houston, Tex.); Isolex available from Medline Industries, Inc. (Mundelein, Ill.); Aqualast™ E0501 available from Lord Corporation (Erie, Pa.); Purforma available from Goodyear (Akron, Ohio), and LIR-700 latex available from Kuraray (Japan). In addition to polyisoprene homopolymers its analogues and derivatives (such as isoprene containing random copolymers, grafting copolymers, cyclized copolymers, chlorinated polyisoprene, hydrogenated polyisoprene, epoxidized polyisoprene, and starcopolymer (dendrimer)), polyisoprene co-polymers and polyisoprene blends can be used as well. Polyisoprene co-polymers which can be used include any co-polymer having an isoprene monomer unit and having sufficiently similar chemical structural and properties of polyisoprene to exhibit the desirable properties of the polyisoprene coating. Suitable polyisoprene blends can include, but are not limited to: natural rubber; polydiene and its co-polymers, such as polybutadiene, styrene butadiene rubber, butadiene co-polymer, substituted polydiene, such as polychloroprene; thermoplastic materials, such as polyurethane; vinyl, nitrile and the like. Combinations of the aforementioned natural rubber and non-natural rubber materials can also be used in conjunction with the polyisoprene latex. As used herein, the term "polyisoprene coating" refers to a coating on a skin contacting surface of an elastomeric article that is greater than about 50% polyisoprene latex.

In one embodiment, no accelerator or cross-linker is used in applying the polyisoprene coating. In another embodiment, an accelerator or cross-linker is used in applying the polyisoprene coating. In such embodiments, any accelerator or cross-linker known in the art can be used to manufacture the polyisoprene latex composition used to coat the elastomeric articles. In a specific embodiment, the polyisoprene latex composition used to coat the elastomeric articles comprises the accelerator composition disclosed in U.S. Patent Publication No. 2004/0169317 (the contents of which are incorporated by reference in their entirety) to increase the rate of vulcanization of the polyisoprene. More than one accelerator can be used. In a specific embodiment, ZDEC, ZMBT, and DPG can be used together as an accelerator (see U.S. Pat. No. 6,828,387 incorporated by reference in its entirety).

As used herein, the term "coating" refers to a thin film of polyisoprene applied to the underlying elastomeric article. In one embodiment, such a coating has a thickness that is at least 10× less than the thickness of the layer of material making up the underlying elastomeric article. In another embodiment, such a coating has a thickness that is at least 100× less than the thickness of the layer of material making up the underlying elastomeric article. Additionally, the polyisoprene coating alters the surface properties of the elastomeric article and may or may not provide a barrier function. The polyisoprene coating of the invention is distinguished from a polyisoprene "layer". Such a layer would be substantially the same thickness as the layer of material making up the underlying elastomeric article. Additionally, a polyisoprene layer would provide a barrier function. The polyisoprene coating on the elastomeric article can be any thickness that is at least 10× thinner than the layer of material making up the elastomeric article providing that the coating imparts improved lubricity of the coated surface and reduced stickiness/tackiness of the coated surface as compared to non-coated surfaces. In one embodiment, the polyisoprene coating is about 1 to about 20 microns, preferably about 5 to about 15 microns, and more preferably either about 8 to about 12 microns or about 5 to about 7 microns in thickness. The total solids content of the polyisoprene composition used for coating can be about 0.5% to about 15%, preferably about 5% to about 8% depending on the thickness of the coating desired.

5.3 Manufacture of Coated Articles of the Invention

The underlying elastomeric article can be made by any method known in the art. Once manufactured, the polyisoprene coating can be applied to the internal surface of the elastomeric article using any method known in the art. Preferred embodiments are disclosed infra.

5.3.1 Manufacture of Elastomeric Article

Porcelain molds (or formers) are cleaned thoroughly, e.g., by one or more of the following steps: (a) mechanically brushing with nylon brushes, (b) dipping into acid solution e.g. citric acid or nitric acid which dissolves residual calcium carbonate powder from the coagulant, (c) mechanically brushing with nylon brushes, (d) dipping into alkaline solution, (e) mechanically brushing with nylon brushes, and (f) dipping into hot water (about 50° C. to about 70° C.) which heat them up to about 60° C. The cleaned molds are dried, e.g., by blowing air onto them and/or placing them into a hot air oven and heating them to about 57° C. to about 61° C.

The cleaned molds are dipped into a coagulant solution (e.g., calcium nitrate and calcium chloride). In embodiments where the coagulant solution is calcium nitrate, the solution is preferably between about 52° C. to about 59° C. with a specific gravity about 1.100 to about 1.200 (depending on the thickness of the material required). The coagulant solution additionally comprises a mold release agent (e.g., calcium carbonate and magnesium carbonate) and a wetting agent (e.g., Surfynol TG and non-ionic surfactants such as Teric 320 and Triton X100). The coagulant-coated molds are dried in an oven (about 100° C. for about 15 seconds) and then dipped into a compounded latex containing a crosslinking agent (e.g., sulfur and a sulfur donor such as tetramethyl thiuram disulfide (TMTD) and tetraethyl thiuram disulfide (TETD)), a vulcanizing accelerator (e.g., zinc dibutyldithiocarbamate (ZDBC), zinc diethyldithiocarbamate (ZDEC), zinc mercaptobenzthiazole (ZMBT), and diphenyl guanidine (DPG)), an activator (e.g., zinc oxide and magnesium oxide), an antioxidant (e.g., Wingstay L and Vulcanox BKF) and, optionally, coloring pigment. The dwell time in the latex is about 10 seconds and the total solids content of the latex varies from about 30% to about 49% depending on thickness required and particular materials used. The latex-coated molds are then passed through one or more, preferably two, hot air ovens to gel the latex film. In one embodiment, water soluble materials (e.g. calcium nitrate, proteins and surfactants) are leached out of the film prior to coating with polyisoprene. In such embodiments, the films are leached in hot water (about 65° C. to about 85° C., preferably in more than one tank, more preferably in five different tanks) for a total of about 4 minutes. In another embodiment, the polyisoprene coating is applied to the film prior to the leaching step (see Section 5.3.2).

In embodiments that the elastomeric article is made of polyisoprene, the manufacturing process described in U.S. Pat. No. 6,828,387 can be used.

5.3.2 Application of Polyisoprene Coating

The polyisoprene coating of the invention can be applied to an elastomeric article by any method known in the art including, but not limited to, dipping, spraying, brushing, flowing, and printing. In preferred embodiments, the polyisoprene coating is applied by single dipping or multiple dipping. Additionally, the polyisoprene coating may be applied to the elastomeric article either prior to or after the leaching step.

In a specific embodiment, the polyisoprene coating is applied by the dipping method.

In more specific embodiments where the polyisoprene coating is applied to the elastomeric article after the leaching step, the leached films are dipped into a polyisoprene latex compound.

In more specific embodiments where the polyisoprene coating is applied to the elastomeric article prior to the leaching step, the latex-coated molds are dipped into the polyisoprene latex composition after drying in the first hot air oven. The molds are then dried in a second hot air oven to gel the latex film. The gelled films are then leached in hot water as described in Section 5.3.1.

After the elastomeric article is coated with the polyisoprene coating, the elastomer and polyisoprene film-coated molds then go into a series of hot air ovens with increasing temperatures from about 115° C. to about 135° C. for about 20 minutes. In the ovens, the elastomeric articles are initially dried and then vulcanized (i.e., the rubber molecules are crosslinked by, e.g., sulfur linkages). The cured elastomeric articles are further leached in hot water and then dipped into a slurry of one or more materials (e.g., calcium carbonate powder or starch powder alone or together and with or without silicone emulsion) that function as a stripping aid and decreases the stickiness of the elastomeric article. After cooling, the elastomeric articles are manually stripped from the molds whereby they are turned inside out thus putting the polyisoprene coating on the inside.

The polyisoprene coating composition can optionally contain curing agents to crosslink the polyisoprene molecules including, but not limited to, sulfur crosslinking system, peroxide crosslinking system (peroxide, hydroperoxide) or prevulcanized/precured polyisoprene molecules with gamma irradiation. Preferably sulfur crosslinking is used. In such embodiments, the crosslinking agents comprise sulfur, vulcanization accelerators, zinc oxide, and an antioxidant. In specific embodiments, the polyisoprene molecules are bonded directly to the rubber surface of the underlying elastomeric article during the crosslinking reaction.

In one embodiment, there is a single coating of polyisoprene applied to the elastomeric article. In other embodiments, more than one coating of polyisoprene is applied to the elastomeric article. In such embodiments, each of the coatings can be identical in composition or they can vary. Additionally, each of the coatings can be of the same thickness or they can vary.

5.3.3 Chlorination

The elastomeric articles of the invention can be post-processed by chlorination which removes powder from the elastomeric article and modifies the internal surface to improve donning and also reduces the grip on the external surface. The formed articles are turned inside out so that the polyisoprene-coated internal surface is on the outside exposed directly to the chlorination. The articles are then loaded into a chlorinator and chlorinated in an aqueous solution of chlorine at a chlorine strength of about 400 ppm to about 700 ppm. At the end of the chlorination cycle, any residual chlorine is neutralized by addition of caustic soda solution such that the pH of the neutralized solution is about 8 and above.

5.3.4 Lubrication

In some embodiments, the elastomeric articles of the invention can further be lubricated after the chlorination process. Lubrication is preferred in order to further improve the ease of donning the elastomeric article of the invention, especially donning of the articles on moist surfaces (damp donning). Any method of lubrication can be used. In one embodiment, the coated elastomeric articles are tumbled with an aqueous solution of the lubricant prior to drying. Any type of lubricant can be used including, but not limited to, a silicone emulsion, a cationic surfactant and with or without an anionic surfactant. In a preferred embodiment, the lubricant comprises cetyl pyridium chloride, silicone SM2140 emulsion and ammonium salt of alkyl phosphate (see, e.g., U.S. patent application Ser. No. 10/666,650).

5.4 Characteristics of the Polyisoprene Coating of the Invention

The polyisoprene coating of the invention displays characteristics that improve the lubricity and reduce the stickiness/tackiness of the coated surface of the elastomeric article.

5.4.1 Soft and Comfortable Feel

The polyisoprene coating of the invention provides a softer and more comfortable feel than uncoated elastomeric articles. This correlates with the modulus values of the coated and uncoated elastomeric articles. Those elastomeric articles with lower modulus values feel more comfortable and softer when donned (see Section 6.9). Polyisoprene coated natural rubber gloves approximated the feel and softness of gloves made entirely from polyisoprene (see Table 6, Sample 2A and Sample 6).

Additionally, the polyisoprene coating of the invention decreases the stickiness of the coated surface of the elastomeric article as compared to an uncoated article (see Section 6.8). Comparison of uncoated natural rubber gloves with polyisoprene coated natural gloves showed a substantial difference in internal stickiness (see Table 5).

Furthermore, the polyisoprene coating of the invention decreases skin irritation from the coated elastomeric article as compared to an uncoated natural rubber article or an article coated with natural rubber.

These characteristics are surprising considering that polyisoprene and natural rubber are very similar chemically. Natural rubber contains about 98% cis-1,4-polyisoprene whilst synthetic polyisoprene contains about 90%-98% cis-1,4-polyisoprene depending on the source of the material and the method of manufacture (P. Henderson, From "Isoprene Monomer to Synthetic Polyisoprene Latex", International Latex Conference, Jul. 25-26, 2000, Akron, Ohio and F. B. Chen, Synthetic Polyisoprene Latex, $3^{rd}$ International Rubber Glove Conference & Exhibition, 12-14 Sep. 2006, Kuala Lumpur, Malaysia).

5.4.2 Rough Surface

Polyisoprene coatings of the invention do not provide a flat surface. Rather, the surface is covered with protrusions of various sizes and shapes extending from the surface. The protrusions measure from about one half micrometer to several micrometers. The protrusions are composed exclusively of the polyisoprene coating material. No additional particles are added to cause the protrusions.

The characteristic of the protrusions can be varied by varying the composition and/or deposition method of the polyisoprene coating.

The protrusions can be seen using a scanning electron microscope at 1000× magnification and/or an Atomic Force Microscope.

5.4.3 Non-Cracking

The polyisoprene coatings of the invention do not show any substantial cracking either when unstretched or when stretched (e.g., 100%, 300%, 500%, etc.). In preferred embodiments, the polyisoprene coating does not show any cracking. As used herein the terms "cracking" or "crack" means a fissure in the surface of the coating that may or may not extend through the entire thickness of the coating to the underlying elastomeric article.

In one embodiment, the coating can be inspected for cracking using a scanning electron microscope at 1000× magnification. In another embodiment, the coating can be inspected for cracking using physical manipulation. In such embodiments, the elastomeric article is stretched (e.g., by 100%, 300%, 500%, etc.) and the coated surface is rubbed repeatedly (e.g. using a finger). In some embodiments, the glove is rubbed using moderate pressure more than 5 times, less than 10 times, less than 20 times, or less than 100 times. The surface is then examined visually for flaking and/or release of a powdery substance which can optionally be made more visible against a black background (e.g., piece of paper or cloth). The presence of flaking and/or the powdery substance indicate the presence of cracking. The polyisoprene coating of the invention shows less cracking and/or flaking as compared to an elastomeric article having an acrylic or a hydrogel coating.

The following examples further illustrate the advantages of the invention and should not be construed as limiting the invention to the embodiments depicted therein.

EXAMPLES

6.1 Example 1

Preparation of a Polyisoprene Coated Glove

A. Glove Production

Porcelain molds (or formers) were cleaned thoroughly by the following steps:

(a) mechanically brushing with nylon brushes, (b) dipping into acid solution e.g. citric acid or nitric acid which dissolves residual calcium carbonate powder from the coagulant, (c) mechanically brushing with nylon brushes, (d) dipping into alkaline solution, and (e) mechanically brushing with nylon brushes.

The molds were further cleaned by dipping into hot water (50-70° C.) which heated them to about 60° C. The cleaned molds were dried by blowing air onto them before placing them into a hot air oven which dried and heated them to 57° C. to 61° C.

The cleaned molds were dipped into calcium nitrate coagulant solution (52-59° C., specific gravity about 1.100-1.200 depending on glove thickness required) which also contained calcium carbonate (mold release agent) and Surfynol TG (wetting agent). The coagulant-coated molds were dried in an oven (100° C. for 15 seconds) and then dipped into a compounded natural rubber containing sulfur (cross-linking agent), zinc dibutyldithiocarbamate (vulcanization accelerator), zinc oxide (activator) and Winstay L (antioxidant) and coloring pigment. The dwell time in the latex was about 10 seconds and the total solids content of the latex varied from 30-49% depending on glove thickness required. The latex-coated molds were then passed through two hot air ovens which gelled the latex film. After that, beads were formed at the end of the cuff area by mechanically rolling down the end portion of the glove. Then the gloves were leached in hot water (65-85° C., in 5 different tanks) for a total of about 4 minutes to leach out water soluble materials e.g. calcium nitrate, proteins and surfactants from the film.

B. Polyisoprene Coating Application

The leached films were then coated with a polyisoprene coating by dipping into a polyisoprene latex compounded using the formulation shown in Table 1 and having a total solids content of 3-15% preferably 5-8%. The latex film-coated molds then were placed into a series of hot air ovens with increasing temperatures from 115° C. to 135° C. for about 20 minutes. In the ovens, the gloves were initially dried and then vulcanization of the rubber occurred whereby the rubber molecules were crosslinked by sulfur linkages. The cured gloves were further leached in hot water to extract more water soluble materials and then dipped into a slurry of calcium carbonate powder or starch powder which functioned as stripping aid as well as prevented the gloves from internally sticking together after stripping. After cooling down, the gloves were manually stripped from the molds whereby they were turned inside out with the polyisoprene coating on the inside.

TABLE 1

| Polyisoprene coating formulation | |
|---|---|
| Ingredients | phr |
| Karton IR-401 RP latex | 100 |
| Soft Water to dilute latex | |
| Sodium caseinate | 0.75 |
| Zinc oxide dispersion | 0.5 |
| Sulfur dispersion | 1.25 |
| Bostex 561 (ZDEC) | 0.5 |
| ZMBT dispersion | 0.5 |
| Bostex 417 (DPG) | 1 |
| Wingstay L | 2 |
| Ammonium hydroxide for adjusting | pH >10.2 |

C. Chlorination

The gloves were post-processed by chlorination. The chlorination process removed powder from the gloves, modified the glove internal surface to improve donning and reduced the grip on the external surface. The formed gloves were manually turned inside out so that the polyisoprene-coated surface was on the outside. The gloves were then loaded into a chlorinator where they were washed by tumbling with water for 3 minutes for two cycles. The gloves were then chlorinated in an aqueous solution of chlorine at a chlorine strength of 400 to 700 ppm for 8.3 minutes. At the end of the chlorination cycle, any residual chlorine was neutralized by addition of caustic soda solution such that the pH of the neutralized solution was about 8 and above. The gloves were tumbled for 4 minutes before the solution was drained off. The gloves were then washed by tumbling with water for five times for three minutes each time.

D. Lubrication

After chlorination, the wet gloves were transferred to a water extraction machine and excess water was removed by centrifuging. In order to improve the donning of the gloves on moist hands (damp donning), the gloves were coated with a lubricant. The gloves were coated by loading the gloves into a washer where they were tumbled with an aqueous solution containing cetyl pyridium chloride (1.56%), silicone SM2140 emulsion (1.5%) and ammonium salt of alkyl phosphate (1.2%). After that, the gloves were dried in a cyclone dryer at about 60° C. for 20 minutes. The partially dried gloves were manually turned inside out and dried further in a cyclone dryer at about 60° C. for another 30 minutes.

6.2 Example 2

Alternative Coating Method

Alternatively, the polyisoprene coating may be applied to the glove before the leaching step. In this case, after the first latex dip and drying in the first hot air oven, the latex-coated molds are dipped into the polyisoprene latex composition and then dried in the second hot air oven to gel the latex film. The gelled films are then beaded before they are leached in hot water. The process continues through vulcanization, post-cure leaching and stripping as described in Section 6.1.

6.3 Example 3

Gloves Used for Testing

A. Natural Rubber Gloves with No Coating

Natural rubber gloves with no coating were prepared as described in Section 6.1 except that the dipping into the polyisoprene latex composition was omitted. The specific gravity of the calcium nitrate coagulant was about 1.144 and the total solids content of the natural rubber was about 47.5%. The gloves produced had a finger thickness of about 0.30 mm. The formed gloves were chlorinated according to the procedure described in Section 6.1 using two different chlorine strengths viz. about 420 ppm and about 550 ppm. After chlorination, the gloves were dried and packed and then evaluated for various properties. Gloves chlorinated at about 420 ppm and about 550 ppm will be referred to as Sample 1A and Sample 1B respectively.

Gloves chlorinated at about 420 ppm also went through the lubrication process described in Section 6.1 and the dried gloves (hereinafter referred to as Sample 10) were packed and evaluated.

B. Natural Rubber Gloves with Polyisoprene Coating

Natural rubber gloves with polyisoprene coating were prepared according to the procedure described in Section 6.1. The specific gravity of the calcium nitrate coagulant was about 1.144 and the natural rubber total solids content was about 47.5%. The total solids content of the polyisoprene coating composition was about 8%. The gloves were coated with a polyisoprene coating after leaching of the natural rubber film. The gloves produced had a finger thickness of about 0.31 mm. The formed gloves were chlorinated according to the procedure described above. Two chlorination levels were investigated viz. chlorine strength of about 420 ppm and about 550 ppm. After chlorination, the gloves were dried, packed and evaluated. Gloves chlorinated at about 420 ppm and about 550 ppm will be referred to as Sample 2A and Sample 2B respectively. Gloves chlorinated at about 420 ppm also went through the lubrication process described above. The dried lubricated gloves (hereinafter referred to as Sample 2C) were packed and evaluated.

C. Acrylic-Coated Natural Rubber Gloves and Non-Coated Natural Rubber Gloves

A sample of a powder-free chlorinated acrylic-coated natural rubber gloves (chlorinated at about 350 ppm chlorine strength, hereinafter referred to as Sample 3) and a sample of the chlorinated non-coated natural rubber gloves (chlorinated at about 350 ppm chlorine strength; hereinafter referred to as Sample 4) were obtained from the same manufacturer. The acrylic-coated gloves (Sample 3) had a finger thickness of about 0.23 mm whilst the non-coated gloves (Sample 4) had a finger thickness of about 0.25 mm. The gloves were evaluated for various properties. The gloves may be prepared by a coating process similar to that described in Section 6.1 but with the polyisoprene latex coating replaced by an acrylic coating having a total solids content of about 1.5% to about 3.5%.

D. Hydrogel-Coated Natural Rubber Gloves

A commercial sample of a powder-free hydrogel-coated natural rubber gloves having a finger thickness of about 0.29 mm (hereinafter referred to as Sample 5) was obtained and evaluated. The gloves were manufactured by Regent Medical, Norcross, Ga. (product ref 30475, lot 04D1482, expiry date April 2009) and were sterile powder-free latex surgical gloves with a "Biogel" coating.

E. Polyisoprene Gloves

Polyisoprene gloves were prepared as described in Section 6.1 except that compounded polyisoprene latex, the formulation shown in Table 1, was substituted for the natural rubber and the total solids content of the latex was about 31.0%. The specific gravity of the calcium nitrate coagulant was about 1.142. The gloves produced had a finger thickness of about 0.28 mm. The formed gloves were chlorinated according to the procedure described in Section 6.1 at a chlorine strength of about 420 ppm. After chlorination, the gloves were dried (hereinafter referred to as Sample 6) and ready for testing.

TABLE 2

Gloves Used for Testing

| Sample Name | Glove | Coating | Example |
|---|---|---|---|
| 1A | natural rubber gloves chlorinated at about 420 ppm | none | 6.2.A |
| 1B | natural rubber gloves chlorinated at about 550 ppm | none | 6.2.A |
| 1C | natural rubber gloves chlorinated at about 420 ppm and lubricated | none | 6.2.A |
| 2A | natural rubber gloves chlorinated at about 420 ppm | polyisoprene coating | 6.2.B |
| 2B | natural rubber gloves chlorinated at about 550 ppm | polyisoprene coating | 6.2.B |
| 2C | natural rubber gloves chlorinated at about 420 ppm and lubricated | polyisoprene coating | 6.2.B |
| 3 | natural rubber gloves chlorinated at about 350 ppm | acrylic | 6.2.C |
| 4 | natural rubber gloves chlorinated at about 350 ppm | none | 6.2.C |
| 5 | natural rubber gloves | hydrogel | 6.2.D |
| 6 | polyisoprene gloves chlorinated at about 420 ppm | none | 6.2.E |

6.4 Example 4

Evaluation by Scanning Electron Microscopy

A. Experimental Design

The surface morphology of the internal surface coating of the following glove samples was examined by scanning electron microscopy at 1000× magnification:

Sample 1A: Natural rubber glove with no coating (control)
Sample 2A: Polyisoprene coating on natural rubber glove
Sample 3: Acrylic coating on natural rubber glove
Sample 5: Hydrogel coating on natural rubber glove For each glove sample, scanning electron micrographs were taken on (a) a sample without stretching, (b) a sample after stretching about 100% for 1 minute and (a) a sample after stretching about 300% for 1 minute.

The scanning electron micrographs of the samples (unstretched and stretched 300%) are shown in FIGS. 1 to 4. Micrographs for samples stretched at about 100% were similar to those stretched at about 300% and were not shown.

B. Observations

Figure 1B:
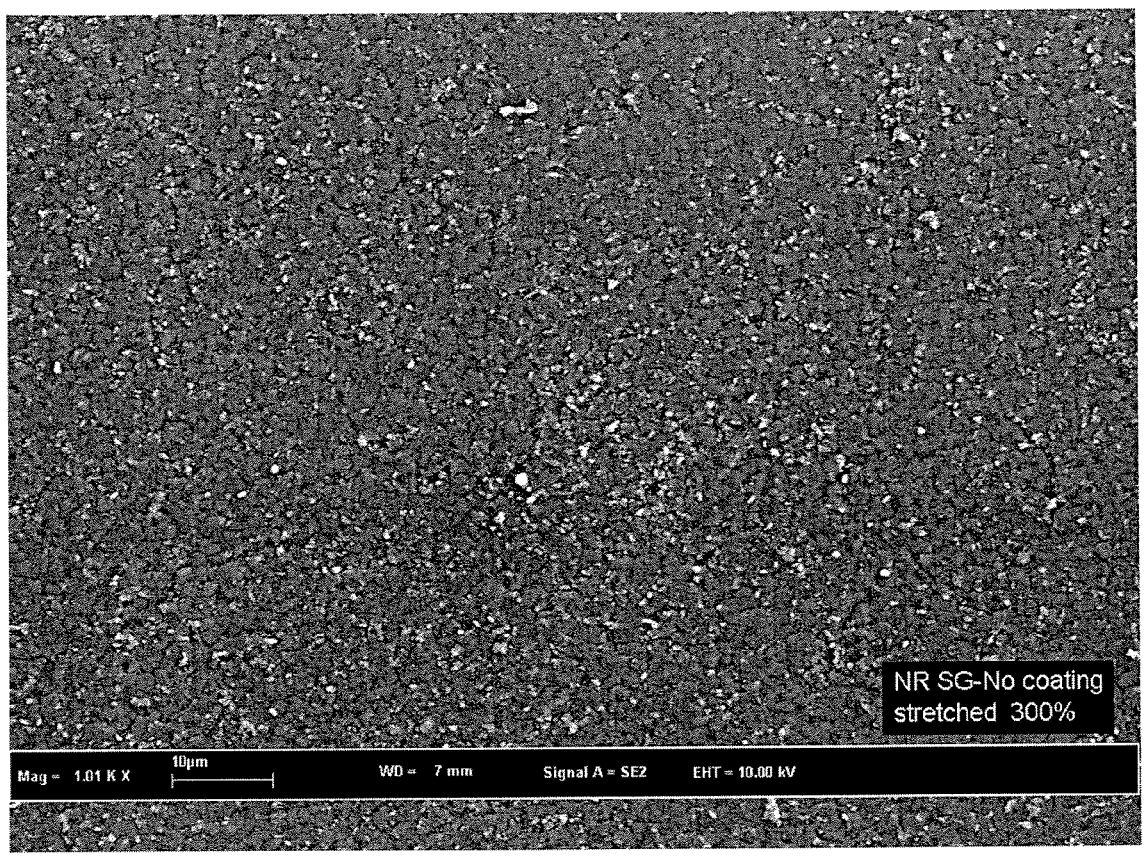

Sample 1A. The surface was essentially quite flat. For the unstretched sample (FIG. 1A) some fine line cracks were discernible. The severity of the cracking was not affected by stretching the sample about 100% or about 300% (FIG. 1B). Cracking of chlorinated natural rubber surface has been reported before (C. C. Ho and M. G. Khew, *International Journal of Adhesion & Adhesives* 19 (1999) 387-398) and the severity of the cracking increased with the extent of chlorination.

Figure 2A:
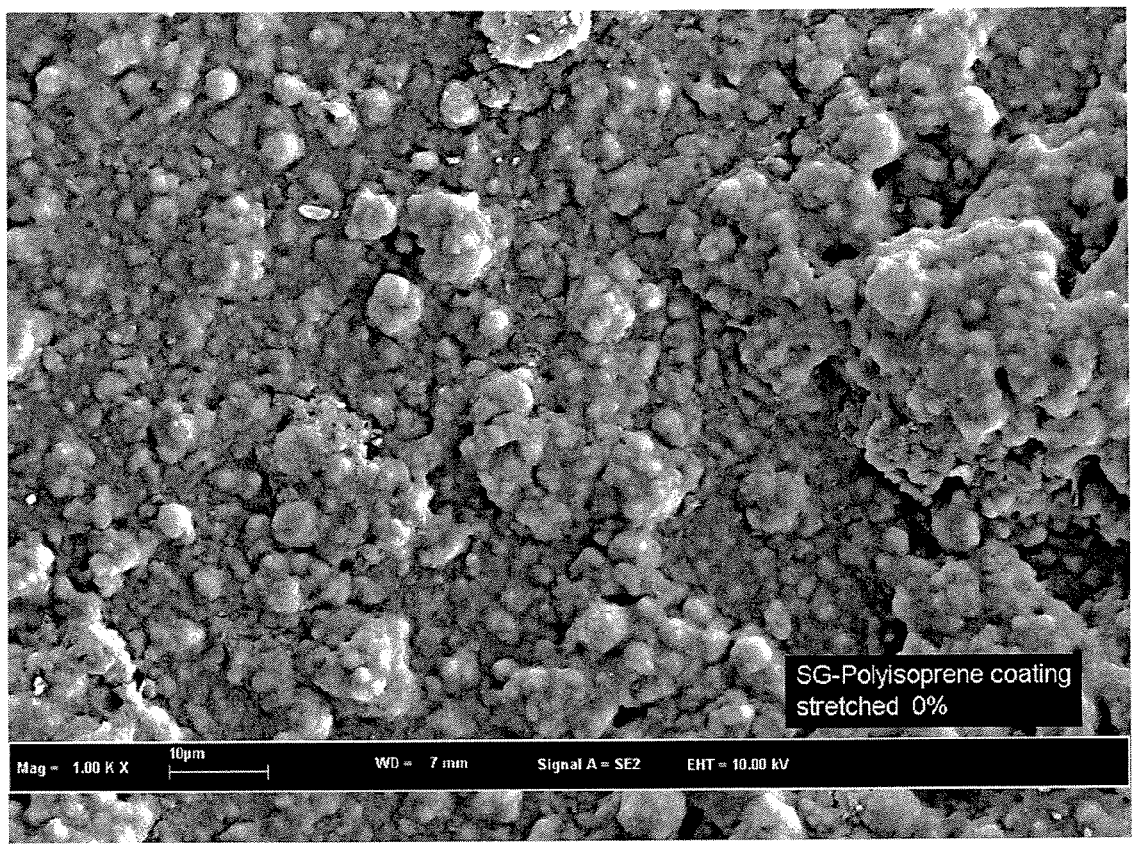
FIGS. 2A-2B show scanning electron micrographs taken on a natural rubber glove with a polyisoprene coating (A) without stretching or (B) after stretching 300% for 1 minute.
Figure 2B:
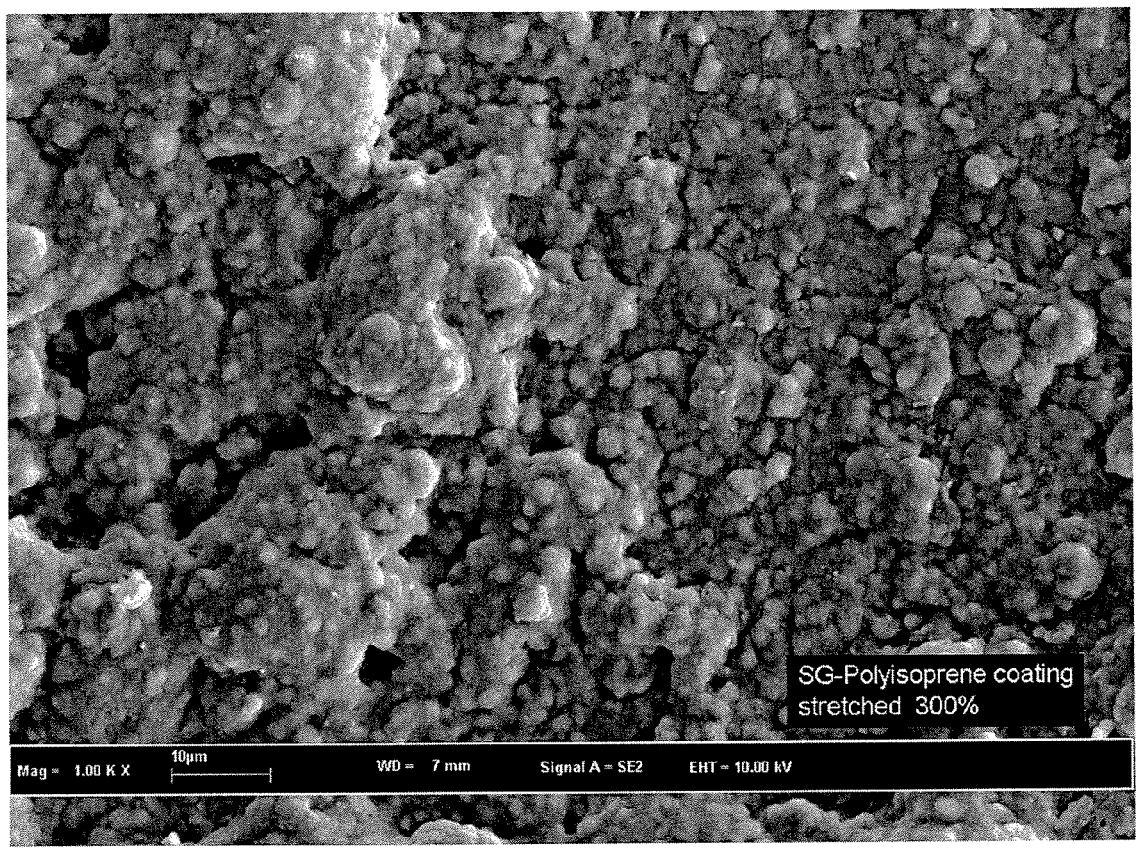

Sample 2A. The most prominent feature of the polyisoprene coating was that the surface was not flat (FIG. 2A). The whole surface was covered with particles of various sizes and shapes protruding from the surface. Some particles (mainly the smaller ones) appeared to be roughly spherical whilst others were irregularly shaped. The bigger protrusions appeared to be made up of aggregates of the smaller particles fused together. The protrusions measured from about half micrometer to several micrometers. No surface cracking was evident for all the samples whether unstretched or after stretching about 300% (FIG. 2B).

Figure 3A:
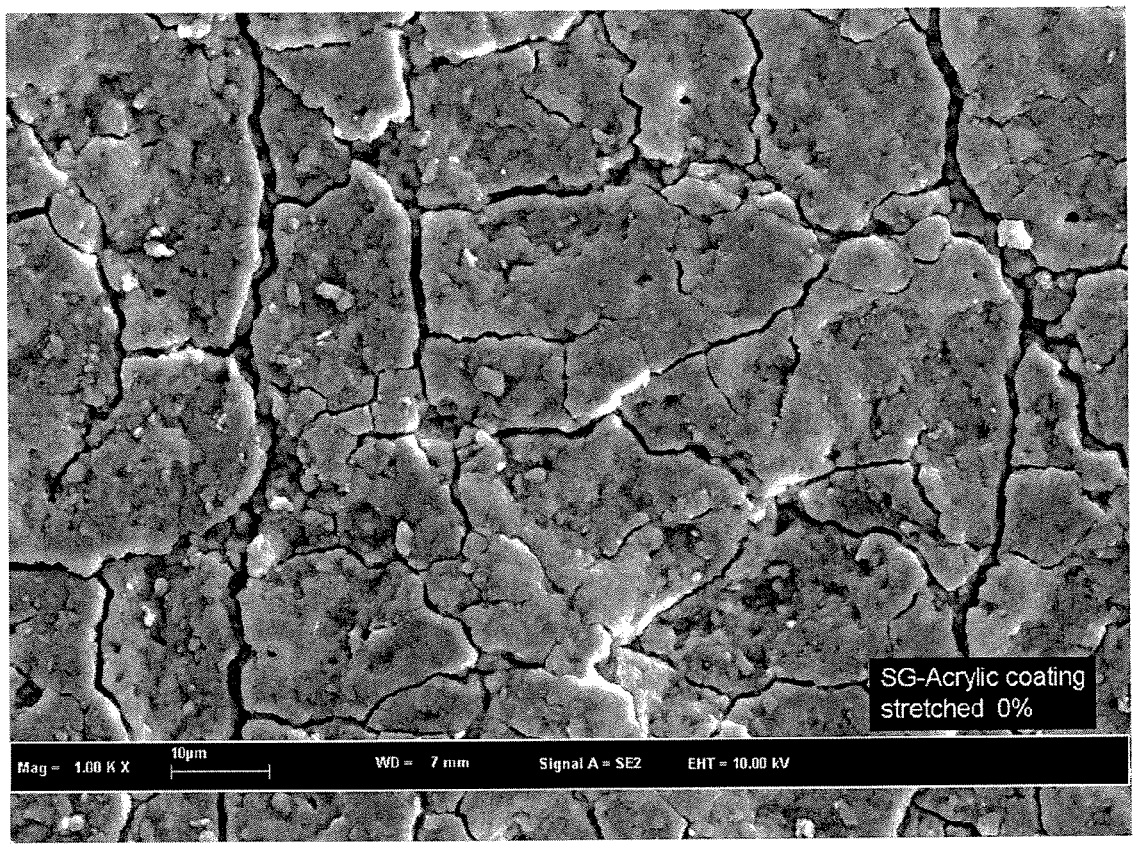
FIGS. 3A-3B show scanning electron micrographs taken on a natural rubber glove with an acrylic coating (A) without stretching or (B) after stretching 300% for 1 minute.
Figure 3B:
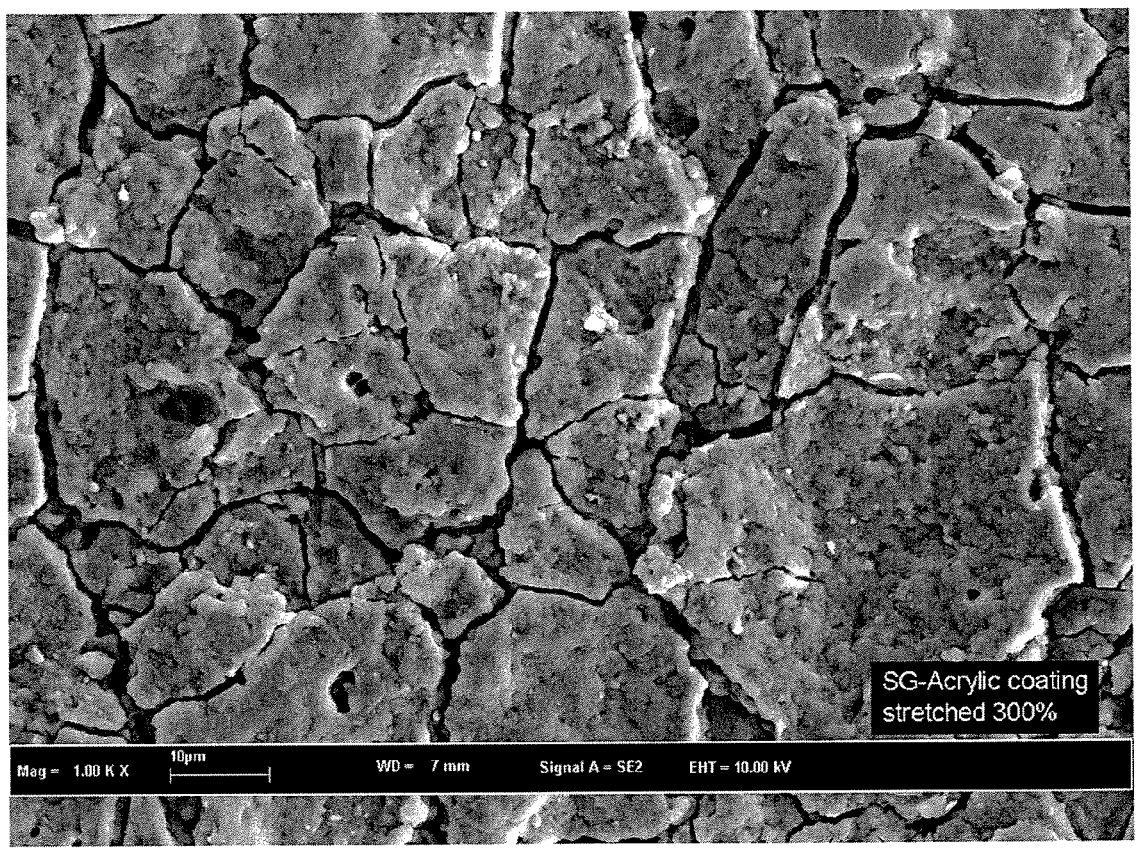

Sample 3. The surface morphology of the samples was essentially quite flat with many cracks such that the surface consists of flakes of acrylic fitted together like a "jig saw puzzle" (FIG. 3A). There appeared to be no difference in the severity of the surface cracking among the samples that was not stretched or stretched to about 100% or about 300% (FIG. 3B).

Figure 4A:
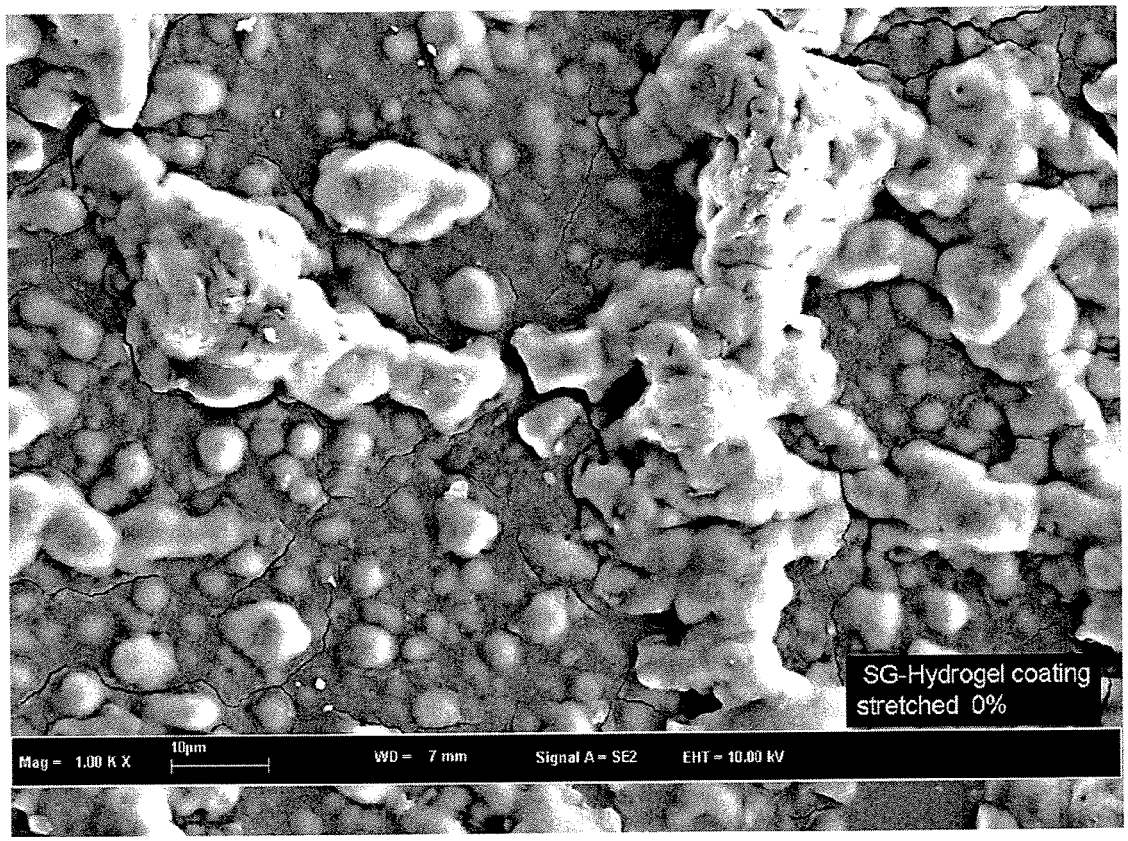
FIGS. 4A-4B show scanning electron micrographs taken on a natural rubber glove with a hydrogel coating (A) without stretching or (B) after stretching 300% for 1 minute.
Figure 4B:
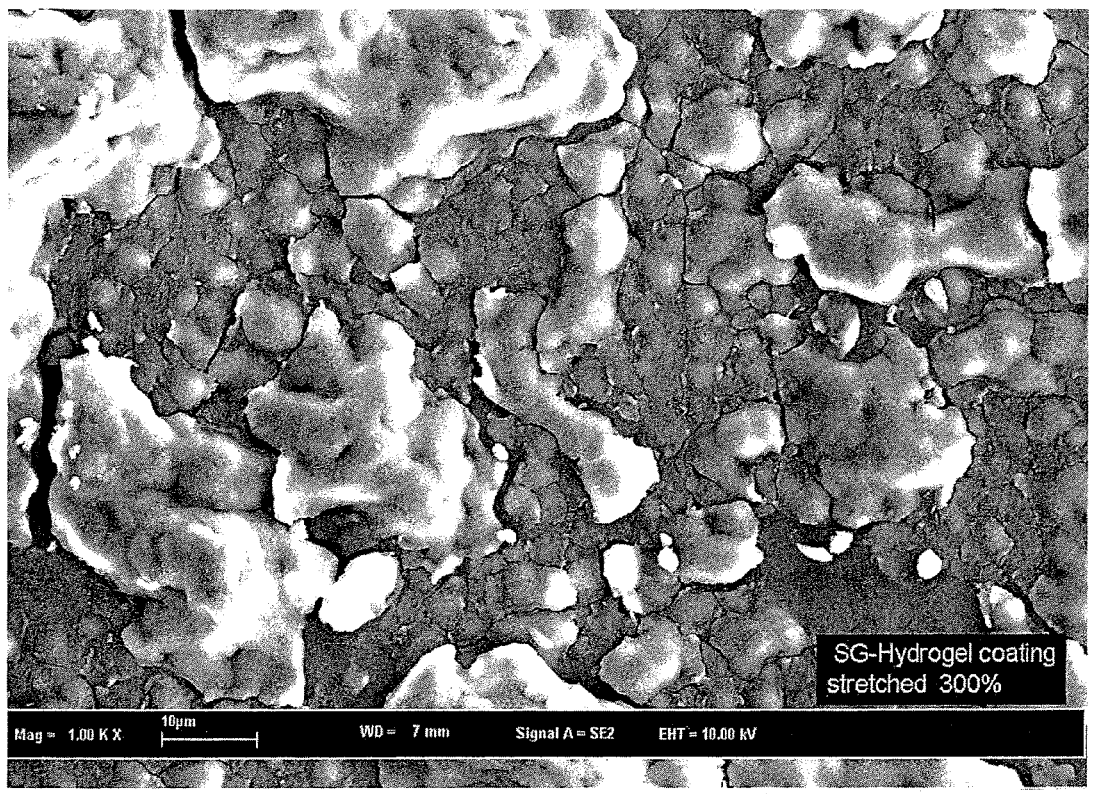

Sample 5. The surface morphology (FIG. 4A) showed some similarity to Sample 2A in that the surface had protrusions. However, there appeared to be less protrusions compared to Sample 2A and the protrusions appeared to have more rounded and smoother surfaces and the sizes of the protrusions were generally bigger. One significant difference was that surface cracks were clearly visible for the unstretched sample as well as for the stretched samples. Samples stretched about 100% and about 300% (FIG. 4B) appeared to have more severe surface cracking than the unstretched sample (FIG. 4A).

Based on the foregoing observations, the polyisoprene coating of the invention does not show any surface cracking for the unstretched gloves as well as for the stretched gloves compared with the prior art coatings which show surface cracks even for the unstretched gloves.

6.5 Example 5

Adhesion of Coating

The adhesion of the polyisoprene coating of the invention, acrylic coating and hydrogel coating to the rubber substrate was evaluated using two samples of each glove type. The finger and palm areas of the glove were stretched to about 500% and the coated surface was rubbed repeatedly using the thumb. The coated surface was then visually examined for coating flakes and powdery substance. The adhesion of the coating was rated qualitatively on a scale of 1 to 5, 1 being the worst case with the entire coating flaking off the rubber substrate and 5 being the best case with no sign of flaking and no visual appearance of powdery substance on the surface of the glove. The adhesion of the polyisoprene coating of the invention was excellent with a rating of 5 (i.e. no flaking or shredding of powder was observed after stretching the glove to about 500% and rubbing it repeatedly with the thumb). The adhesion of the acrylic coating (Sample 3) and hydrogel coating (Sample 5) was about the same with a rating of 4. In both cases, some whitish flakes came off the gloves after stretching the glove to about 500% and rubbing repeatedly with the thumb.

The above results for the polyisoprene coating of the invention correlated well with the pictures of the surface coating from scanning electron microscopy which showed no cracking on the surface for the unstretched sample as well as for the stretched samples. The high ultimate elongation of the polyisoprene coating (which was higher than that of the natural rubber base glove) could explain why no cracking was observed when the glove was stretched to about 500%.

It could also be concluded that bonding of the polyisoprene coating to the natural rubber substrate (which is chemically similar i.e. also polyisoprene) was very good.

As noted earlier, the scanning electron micrographs of both the acrylic coated and hydrogel coated gloves showed surface cracking for the unstretched as well as for the stretched samples. The cracking could lead to delamination of the coating which appeared as flaking of the coating from the substrate.

6.6 Example 6

Donning of Unlubricated Gloves

Gloves without lubricant were donned by a panel of three researchers who routinely work with gloves on dry hands and subjectively assessed for the ease of donning on a scale of 1 to 5, in which 1 means very difficult to don and 5 means very easy to don. The results (Table 3) show that compared with uncoated natural rubber glove the polyisoprene coated glove provides significantly better donning performance. Without being bound by any particular theory, it is believed that polyisoprene is much more sensitive to chlorination than natural rubber which creates a better textured protrusions on the glove surface resulting in a lower friction force during donning.

Additionally, the polyisoprene coating can comply with chlorination process characterized by different chlorine strength, e.g., from 420 ppm to 550 ppm and provides consistent better donnability than uncoated natural rubber glove.

TABLE 3

| Dry Donning of Gloves | |
|---|---|
| Glove Sample | Dry Donning Rating |
| 2A (NR glove, polyisoprene coated) at 420 ppm | 4.5 |
| 1A (NR glove, uncoated) at 420 ppm | 1 |
| 2B (NR glove, polyisoprene coated) at 550 ppm | 5 |
| 1B (NR glove, uncoated) at 550 ppm | 2 |

6.7 Example 7

Donning of Lubricated Gloves

Gloves treated with lubricant were donned on dry hands as well as on moist/damp hands and subjectively assessed for ease of donning by a panel of three researchers who routinely work with gloves on a scale of 1 to 5, in which 1 means very difficult to don and 5 means very easy to don. The results (Table 4) showed that the polyisoprene coating improved the donnability of the gloves (relative to the uncoated gloves) on dry hands as well as on damp hands. Treatment of the uncoated gloves with lubricant improved the donnability of the gloves on damp hands compared with on dry hands but the damp donning rating was still significantly poorer than that of the lubricated polyisoprene coated gloves (Sample 2C). Without being bound by any particular theory, it is postulated that the higher chlorination efficiency of polyisoprene coating, showed in Example 6 above, can further comply with lubrication process providing better damp donning than uncoated natural rubber glove. Accordingly, the use of lower level ppm of chlorination on the polyisoprene coated glove will exhibit less surface damage while having the advantages the chlorination treatment.

TABLE 4

Donning of Lubricated Gloves

| Glove ID | Dry Donning Rating | Damp Donning Rating |
|---|---|---|
| 2C (polyisoprene coated) | 4.5 | 4.5 |
| 1C (uncoated) | 1 | 2.5 |

6.8 Example 8

Internal Stickiness

Gloves were packed and sterilized by gamma-radiation at about 29.5 kGy to about 30.3 kGy. The sterilized gloves were aged at about 70° C. for 1 day and 7 days and evaluated to assess the extent that the internal surfaces of the gloves stick to each other, also referred to as blocking. The degree of stickiness was rated on a scale of 1 to 5 with 1 representing not sticking at all and 5 representing seriously sticking to each other. Results are shown in Table 5.

The results demonstrate that the inventive polyisoprene coating did not show any stickiness even after aging for 7 days at about 70° C. compared with the uncoated natural rubber surface which showed serious blocking even after 1 day aging at about 70° C. Without being bound by any particular theory, it is postulated that the protrusions on the chlorinated surface of the polyisoprene coating reduces the surface area for contact and hence reduces the tendency for the surfaces sticking to each other.

TABLE 5

Internal Stickiness

| | Internal Stickiness Rating | |
|---|---|---|
| Glove ID | Aged 70° C./1 day | Aged 70° C./7 days |
| Sample 2A (polyisoprene coated) | 1 | 1 |
| Sample 1A (uncoated) | 4.5 | 4.5 |
| Sample 2B (polyisoprene coated) | 1 | 1 |
| Sample 1B (uncoated) | 4.5 | 4.5 |

6.9 Example 9

Physical Properties and Glove Touch Feel

The modulus at different elongation were determined and the results shown in Table 6.

Generally, the feeling (after donning) of softness/stiffness of uncoated rubber gloves of similar thickness may be correlated with the modulus values of the rubber e.g. glove with a soft feel would have a lower modulus than a glove with a stiffer feel. For gloves with a coating, the feel of the glove after donning would be expected to be governed mainly by the modulus of the coating material since it is the latter that is in direct contact with the skin.

Sample 3 (acrylic-coated) and Sample 4 (uncoated) gloves were donned and evaluated by a panel of three researchers who routinely work with gloves. The results showed that Sample 3 definitely felt stiffer than Sample 4. In fact, the panel reported that the stiffness of the acrylic coating can be felt by the hands. The feeling of softness/stiffness of the gloves actually correlated with the modulus values of the gloves i.e. Sample 3 had higher modulus values than Sample 4. It was not expected that a thin coating could affect the modulus of the whole glove unless (1) the modulus of the acrylic coating was very high and/or (2) the coating was not very thin.

Uncoated polyisoprene gloves (Sample 6) and uncoated natural rubber gloves (Sample 1A) were donned and evaluated by the same panel of people. The results showed that uncoated polyisoprene gloves definitely felt softer than the uncoated natural rubber gloves. This was expected and correlated well with the modulus values of the gloves i.e. polyisoprene gloves had significantly lower modulus values than natural rubber gloves.

Polyisoprene-coated gloves (Sample 2A) and uncoated natural rubber gloves (Sample 1A) were donned and evaluated by the same panel of people. The results showed that polyisoprene-coated gloves were judged as softer than or similar to uncoated natural rubber gloves. This correlated well with the modulus values of the two glove samples despite the fact that the modulus values (M100 and M300) of the polyisoprene-coated gloves were only slightly lower than those of the uncoated gloves.

| Sample ID | M100% kg/cm$^2$ | M300% kg/cm$^2$ | M500% kg/cm2 |
|---|---|---|---|
| Sample 3 (acrylic coated) | 13 | 24 | 54 |
| Sample 4 (uncoated) | 10 | 18 | 33 |
| Sample 1A (uncoated) | 8 | 15 | 33 |
| Sample 2A (polyisoprene coated) | 7 | 13 | 28 |
| Sample 6 (Polyisoprene) | 5 | 10 | 20 |

6.10 Example 10

Natural Rubber Gloves with an Alternate Polyisoprene Coating

Natural rubber gloves with an alternate polyisoprene coating that was formulated differently than in Sections 6.1 were prepared in the laboratory according to the procedure described in Section 6.1. The coating composition is given in Table 7. The specific gravity of the calcium nitrate coagulant was 1.150 and the NR latex total solids content was 47.5%. The total solids content of the polyisoprene coating composition was 8%. The gloves were coated with a polyisoprene coating after leaching of the NR latex film. The gloves were cured for 30 minutes at 135° C. The gloves produced had a finger thickness of 0.30 mm. The formed gloves were chlorinated at 420 ppm according to the procedure described in Section 6.1. After chlorination, the gloves were dried, packed and evaluated.

Gloves were donned on dry hands and subjectively assessed for the ease of donning on a scale of 1 to 5, in which 1 means very difficult to don and 5 means very easy to don.

The gloves had a donning rating of 4.5 which was similar to that of gloves coated with 100% polyisoprene (Sample 2A in Table 3).

Packed gloves were aged at 70° C. for 1 day and 7 days and evaluated for the extent the internal surfaces of the gloves stuck to each other. The degree of stickiness was rated on a scale of 1 to 5 with 1 representing not sticking at all and 5 representing seriously sticking to each other. The gloves did not stick to each other at all on the internal surface after aging 1 day at 70° C. as well as after aging 7 days at 70° C. The internal stickiness ratings were 1 for both aging conditions. These results were similar to those of gloves coated with 100% polyisoprene (Sample 2A in Table 5).

The adhesion of the alternate polyisoprene coating to the rubber substrate was evaluated. The finger and palm areas of the glove were stretched to about 500% and the coated surface was repeatedly rubbed using the thumb. The coated surface was then visually examined for coating flakes and powdery substance. The adhesion of the coating was rated qualitatively on a scale of 1 to 5, 1 being the worst case with the entire coating flaking off the rubber substrate and 5 being the best case with no sign of flaking and no visual appearance of powdery substance on the surface of the glove. The adhesion of the alternate polyisoprene coating was excellent with a rating of 5 (i.e. no flaking or shredding of powder was observed after stretching the glove to 500% and rubbing it repeatedly with the thumb). The adhesion of the alternate polyisoprene coating is similar to that of the 100% polyisoprene coating (see Section 6.5).

TABLE 7

Alternate Polyisoprene coating formulation

| Ingredients | phr |
| --- | --- |
| Kraton IR-401 RP PI latex | 100 |
| Soft water to dilute latex | |
| Sodium caseinate | 0.75 |
| Zinc Oxide Dispersion | 0.5 |
| Sulfur Dispersion | 1.5 |
| ZDBC Dispersion | 1 |
| Wingstay L | 2 |
| Ammonium Hydroxide for adjusting | pH >10.2 |

6.10 Example 11

Natural Rubber Gloves with a Polyisoprene Blend Coating

Natural rubber gloves with a coating comprising a blend of 90% polyisoprene (PI) and 10% nitrile were prepared in the laboratory according to the procedure described in Section 6.1. The coating composition is given in Table 7 and is similar to the coating composition that was given in Table 1 except that the Kraton IR-401 RP polyisoprene latex was replaced by a blend comprising 90% polyisoprene and 10% Reichhold nitrile 68077-01 latex. The specific gravity of the calcium nitrate coagulant was 1.150 and the NR latex total solids content was 47.5%. The total solids content of the polyisoprene/nitrile blend coating composition was 8%. The gloves were coated with a polyisoprene/nitrile coating after leaching of the NR latex film. The gloves were cured for 30 minutes at 135° C. The gloves produced had a finger thickness of 0.31 mm. The formed gloves were chlorinated at 420 ppm according to the procedure described in Section 6.1. After chlorination, the gloves were dried, packed and evaluated.

Gloves were donned on dry hands and subjectively assessed for the ease of donning on a scale of 1 to 5, in which 1 means very difficult to don and 5 means very easy to don. The gloves had a donning rating of 4.5 which was similar to that of gloves coated with 100% polyisoprene (Sample 2A in Table 3).

Packed gloves were aged at 70° C. for 1 day and 7 days and evaluated for the extent the internal surfaces of the gloves stuck to each other. The degree of stickiness was rated on a scale of 1 to 5 with 1 representing not sticking at all and 5 representing seriously sticking to each other. The gloves were not sticking to each other at all on the internal surface after aging 1 day at 70° C. as well as after aging 7 days at 70° C. The internal stickiness ratings were 1 for both aging conditions. These results were similar to those of gloves coated with 100% polyisoprene (Sample 2A in Table 5).

The adhesion of the inventive polyisoprene/nitrile blend coating to the rubber substrate was evaluated. The finger and palm areas of the glove were stretched to about 500% and the coated surface was repeatedly rubbed using the thumb. The coated surface was then visually examined for coating flakes and powdery substance. The adhesion of the coating was rated qualitatively on a scale of 1 to 5, 1 being the worst case with the entire coating flaking off the rubber substrate and 5 being the best case with no sign of flaking and no visual appearance of powdery substance on the surface of the glove. The adhesion of the inventive polyisoprene/nitrile blend coating was excellent with a rating of 5 i.e. no flaking or shredding of powder was observed after stretching the glove to 500% and rubbing it repeatedly with the thumb. The adhesion of the polyisoprene/nitrile coating is similar to that of 100% polyisoprene coating (see Section 6.5 or 6.10).

TABLE 8

Polyisoprene/nitrile coating formulation

| Ingredients | phr |
| --- | --- |
| Kraton IR-401 RP PI latex | 90 |
| Reichhold Nitrile 68077-01 | 10 |
| Soft water to dilute latex | |
| Sodium caseinate | 0.75 |
| Zinc Oxide Dispersion | 0.5 |
| Sulfur Dispersion | 1.25 |
| Bostex 561 (ZDEC) | 0.5 |
| ZMBT dispersion | 0.5 |
| Bostex 417 (DPG) | 1 |
| Wingstay L | 2 |
| Ammonium Hydroxide for adjusting | pH >10.2 |

INDUSTRIAL APPLICABILITY

The invention is useful in a manufacturing process for elastomeric articles composed of natural rubber, synthetic polyisoprene, synthetic polymers such as neoprene, polyurethane, nitrile, vinyl, styrene butadiene and co-polymer of butadiene. The invention affords the ability to produce the elastomeric articles with a polyisoprene coating whereby the coated surfaces have no or reduced stickiness/tackiness and improved lubricity. The invention can be advantageously incorporated into the manufacturing of surgical gloves, condoms, probe covers, dental dams, finger cots, catheters, and the like.

The invention has been described with reference to various specific and preferred embodiments and techniques. However, it should be understood that many variations and modifications can be made while remaining within the spirit or scope of the invention as defined by the claims set forth below.

What is claimed is:

1. A coated elastomeric rubber article comprising:
an elastomeric rubber article having a first surface, and
a coating formed from a coating composition comprising synthetic polyisoprene rubber,
wherein the coating is provided on at least a portion of the first surface of the elastomeric rubber article, and
wherein the coating has protrusions made from the coating composition.

2. The coated elastomeric rubber article of claim 1, wherein the coating is directly bonded to the first surface of the elastomeric rubber article.

3. The coated elastomeric rubber article of claim 1, wherein the elastomeric rubber article is made from natural rubber, synthetic polyisoprene, polychloroprene, nitrile, carboxylated acrylonitrile butadiene rubber, styrene butadiene rubber, butadiene co-polymer, polyurethane, vinyl, or mixtures thereof.

4. The coated elastomeric rubber article of claim 1, wherein the coating composition further comprises natural rubber latex, polychloroprene latex, nitrile latex, carboxylated acrylonitrile butadiene rubber latex, styrene butadiene latex, butadiene co-polymer latex, polyurethane latex, or polyvinyl chloride latex.

5. The coated elastomeric rubber article of claim 1, wherein the coated elastomeric rubber article is treated with a lubricant solution.

6. The coated elastomeric rubber article of claim 1, wherein the protrusions are in the range of 0.5 microns to 10 microns.

7. The coated elastomeric rubber article of claim 1, wherein the protrusions do not contain additional particles.

8. The coated elastomeric rubber article of claim 1, wherein the protrusions comprise synthetic polyisoprene rubber.

9. The coated elastomeric rubber article of claim 1, wherein the first surface is an internal surface of the elastomeric rubber article.

10. The coated elastomeric rubber article of claim 9, wherein the elastomeric rubber article is a glove, tube, condom, probe cover, dental dam, finger cot, film, shunt, valve, stent, or implant.

11. The coated elastomeric rubber article of claim 1, wherein the first surface is an external surface of the elastomeric rubber article.

12. The coated elastomeric rubber article of claim 11, wherein the elastomeric rubber article is a catheter.

13. The coated elastomeric rubber article of claim 1, wherein the coated elastomeric rubber article exhibits at least one of improved dry skin lubricity, improved damp skin lubricity, decreased stickiness, increased comfort, increased softness, decreased modulus value, decreased skin irritation, decreased cracking of at least one of an elastomeric surface and the coating when stretched, and decreased flaking of at least one of the elastomeric surface and the coating when stretched as compared to an elastomeric rubber article that comprises the same elastomeric material but is not coated with a coating composition comprising synthetic polyisoprene rubber.

14. The coated elastomeric rubber article of claim 1, wherein the coating composition used to form the coating has a total solids content of from about 3% to about 15%.

15. The coated elastomeric rubber article of claim 1, wherein the coating composition used to form the coating has a total solids content of from about 5% to about 8%.

16. The coated elastomeric rubber article of claim 1, wherein the coated elastomeric rubber article is chlorinated.

17. The coated elastomeric rubber article of claim 1, wherein the coating composition further comprises a curing agent, and wherein the synthetic polyisoprene rubber is crosslinked to the rubber of the elastomeric rubber article.

18. The coated elastomeric rubber article of claim 17, wherein the curing agent comprises at least one of sulfur, a sulfur donor, a vulcanization accelerator, an activator, and an antioxidant.

19. The coated elastomeric rubber article of claim 18, wherein the sulfur donor is selected from the group consisting of tetramethyl thiuram disulfide (TMTD) and tetraethyl thiuram disulfide (TETD).

20. The coated elastomeric rubber article of claim 18, wherein the vulcanization accelerator is selected from the group consisting of zinc dibutyldithiocarbamate (ZDBC), zinc diethyldithiocarbamate (ZDEC), zinc mercaptobenzthiazole (ZMBT), and diphenyl guanidine (DPG).

21. The coated elastomeric rubber article of claim 18, wherein the antioxidant is selected from the group consisting of

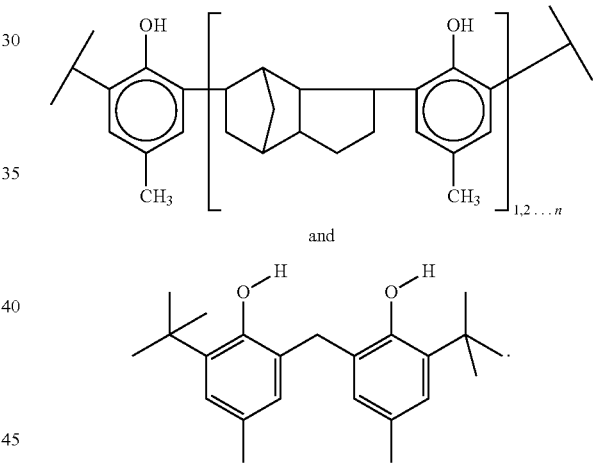

22. The coated elastomeric rubber article of claim 18, wherein the activator is selected from the group consisting of zinc oxide and magnesium oxide.

23. A coated elastomeric rubber article comprising:
an elastomeric rubber article having an internal surface and an external surface, and
a coating formed from a coating composition comprising synthetic polyisoprene rubber,
wherein the coating is provided on at least a portion of the internal surface of the elastomeric rubber article or at least a portion of the external surface of the elastomeric rubber article, and
wherein the coating has protrusions made from the coating composition.

24. The coated elastomeric rubber article of claim 23, wherein the coating is provided on at least a portion of the internal surface of the elastomeric rubber article.

25. A coated elastomeric rubber article comprising:
an elastomeric rubber article having a skin-contacting surface, and a coating formed from a coating composition comprising synthetic polyisoprene rubber, wherein the coating is provided on at least a portion of the skin-contacting surface of the elastomeric rubber article, and wherein the coating has protrusions made from the coating composition.

26. The coated elastomeric article of claim 1, wherein the coating is applied by dipping, spraying, brushing, flowing or printing.

* * * * *